United States Patent
Kinoshita et al.

(10) Patent No.: US 8,172,822 B2
(45) Date of Patent: May 8, 2012

(54) WEARING ARTICLE AND METHOD OF MAKING THE SAME

(75) Inventors: Akiyoshi Kinoshita, Kagawa (JP); Kayoko Tanaka, Kagawa (JP); Yasuhiko Kenmochi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 12/992,343

(22) PCT Filed: Mar. 23, 2009

(86) PCT No.: PCT/JP2009/055601
§ 371 (c)(1),
(2), (4) Date: Nov. 12, 2010

(87) PCT Pub. No.: WO2009/139226
PCT Pub. Date: Nov. 19, 2009

(65) Prior Publication Data
US 2011/0066129 A1    Mar. 17, 2011

(30) Foreign Application Priority Data
May 15, 2008    (JP) ................. 2008-128915

(51) Int. Cl.
*A61F 13/62* (2006.01)
*A41K 37/02* (2006.01)

(52) U.S. Cl. ........................ 604/391; 156/66

(58) Field of Classification Search .......... 604/391, 604/387, 389, 386; 156/66
See application file for complete search history.

(56) References Cited

U.S. PATENT DOCUMENTS

| 5,897,545 A | * | 4/1999 | Kline et al. ............ 604/386 |
| 6,540,497 B1 | | 4/2003 | Fuda et al. |
| 2006/0096072 A1 | | 5/2006 | Minato et al. |

FOREIGN PATENT DOCUMENTS

| JP | 01-156502 | 6/1989 |
| JP | 2000-225650 | 8/2000 |
| JP | 2002-532195 A | 10/2002 |
| JP | 2004-097384 | 4/2004 |
| JP | 2006-055669 | 3/2006 |
| WO | WO 00/37009 | 6/2000 |

OTHER PUBLICATIONS

International Search Report from corresponding PCT application No. PCT/JP2009/055601 dated Jun. 23, 2009, 4 pages.

* cited by examiner

*Primary Examiner* — Lynne Anderson
*Assistant Examiner* — Bradley Philips
(74) *Attorney, Agent, or Firm* — Brinks Hofer Gilson & Lione

(57) ABSTRACT

A wearing article configured so that hook elements of a mechanical fastener can be firmly attached to a chassis and the hook elements can be held in engagement with loop elements of a mechanical fastener tightly without correspondingly increasing a manufacturing cost. The wearing article has front and rear waist regions that respectively include a first pair of lateral zones and a second pair of lateral zones, these lateral zones in each pair are opposed to each other in a transverse direction X and extending in a longitudinal direction Y. An inner sheet is provided in the first lateral zones with mount members attached thereto and hook elements are attached to the diaper via the mount members. In the second lateral zones, the inner sheet is provided with loop elements attached thereto. First and second arrays of the hook elements include deformed regions created over the entire areas thereof by pressure-treatment.

17 Claims, 6 Drawing Sheets

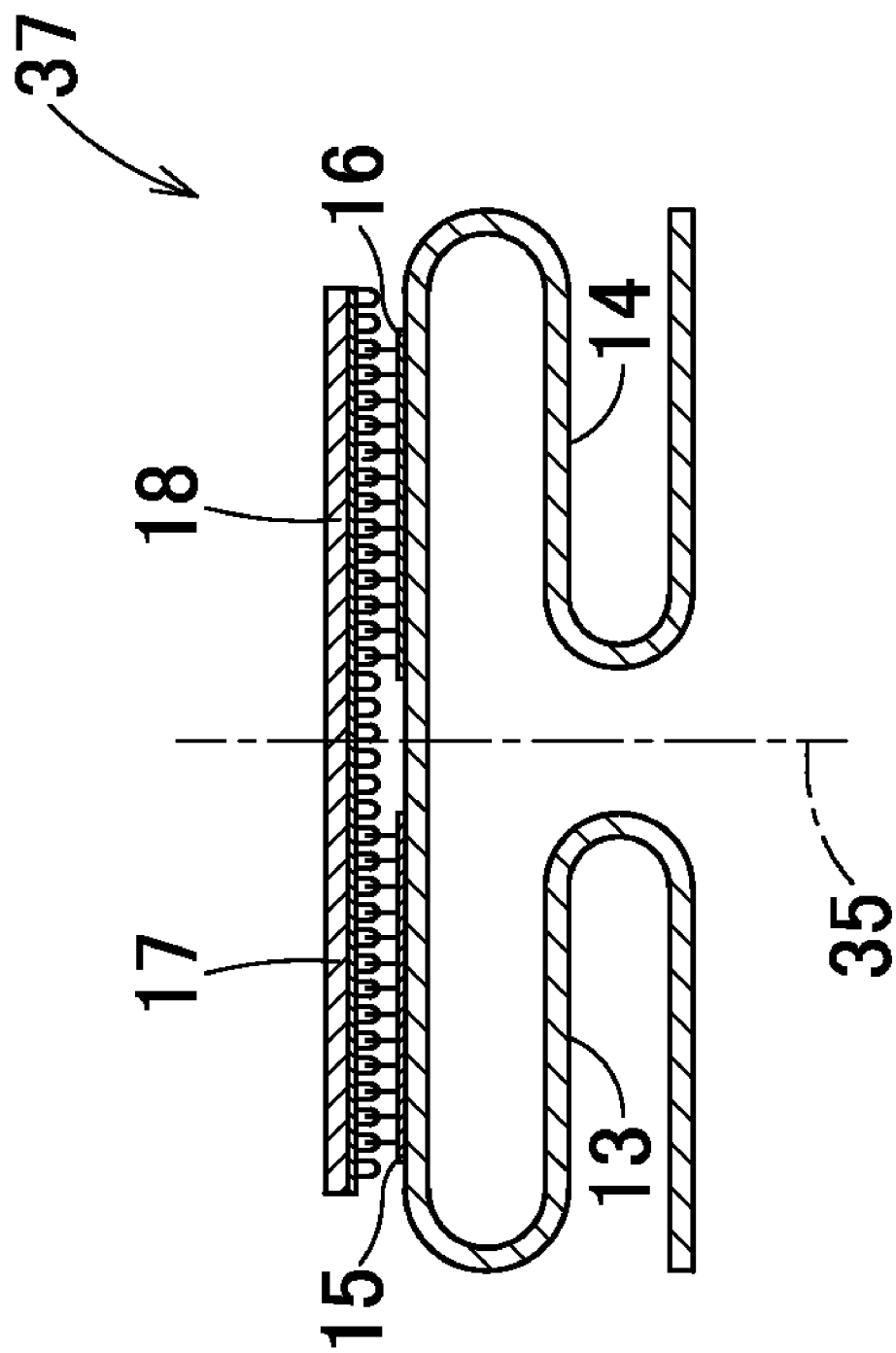

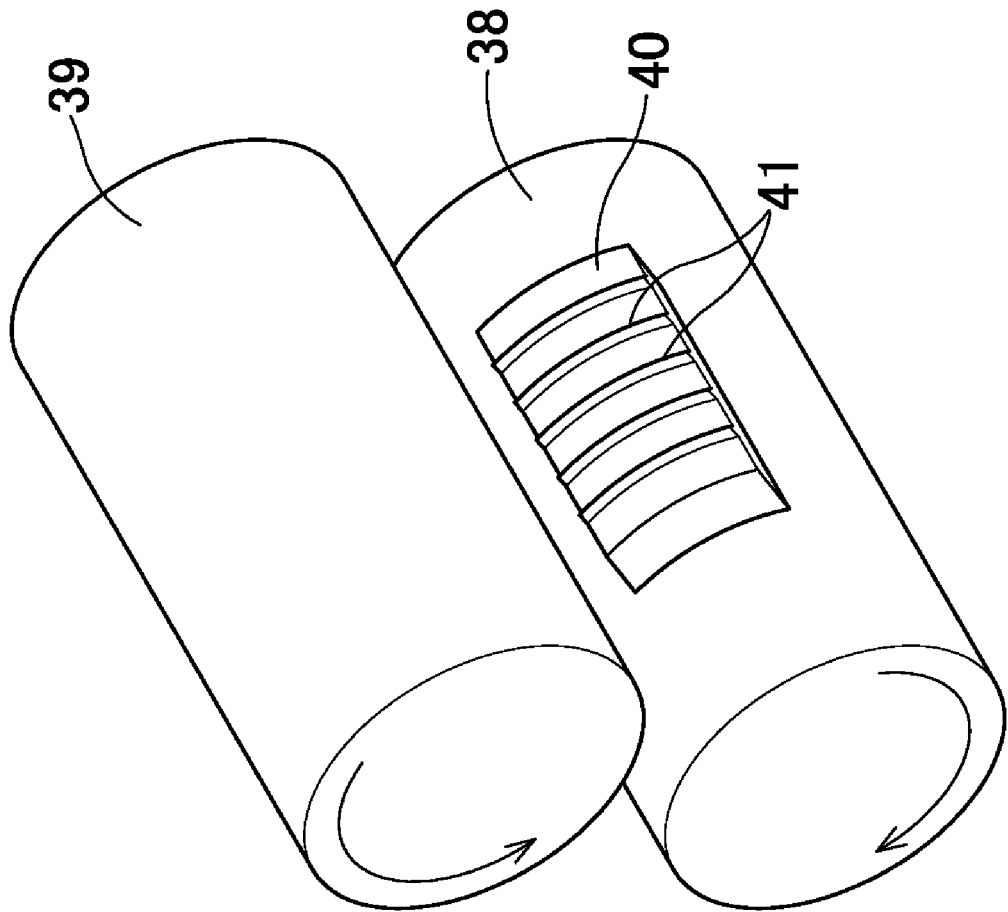

WEARING ARTICLE AND METHOD OF MAKING THE SAME

RELATED APPLICATION

This application is a 35 U.S.C. §371 national phase filing of International Patent Application No. PCT/JP2009/055601, filed Mar. 23, 2009, through which and to which priority is claimed under 35 U.S.C. §119 to Japanese Patent Application No. 2008-128915, filed May 15, 2008.

TECHNICAL FIELD

The present invention relates to wearing articles and more particularly to wearing articles such as disposable diapers, toilet training pants, incontinent briefs, or diaper covers and a method of making the same.

RELATED ART

Disposable diapers having front and rear waist regions adapted to be detachably engaged with each other along respective pairs of transverse opposite lateral zones thereof are known. For example, one of such diapers is disclosed in Publication of JP 2006-55669 T (PATENT DOCUMENT 1). According to the disclosure of this PATENT DOCUMENT 1, the diaper comprises a chassis including a front region, a rear waist region and a crotch region, and a pair of ear-like panels extending outward from the respective lateral zones of the rear waist region. The ear-like panels are provided with hook members adapted to be engaged with loop members on the front waist region so that the front and rear waist regions may be connected to each other along the lateral zones thereof and the diaper may be shaped into a pant.
[PATENT DOCUMENT 1] JP 2006-55669 T

DISCLOSURE OF THE INVENTION

Problem to be Solved by the Invention

The hook member is attached to the ear-like panel by interposing an adhesive between the hook member and the ear-like panel and further by partially heat-treating the hook member and the ear-like panel under pressure along outer edge of the hook member. Thus the hook member is bonded to the ear-like panel by the adhesive and, in addition, partially fusion bonded to the ear-like panel by a heat-treatment under pressure so that the hook member and the ear-like panel would be bonded to each other as tightly as possible. However, the hook member may be partially deformed due to thermal fusion and such deformed portion may lose its function of engagement. In consequence, a total effect of engagement between the hook member and the loop member may be deteriorated. To compensate the deteriorated effect of engagement, respective areas of the hook member and the loop member must be enlarged and a correspondingly increased cost must be accepted. Furthermore, the heat treatment under pressure carried out along the outer edge of the hook member as has been described above will require a high degree of precision inevitably resulting in deterioration of production speed which may, in turn, lead to an increase of the manufacturing cost.

In view of the problem as has been described above, it is an object of the present invention to provide a wearing article improved so that hook elements of a mechanical fastener can be firmly attached to a chassis and the hook elements can be held in engagement with loop members of the mechanical fastener tightly without correspondingly increasing a manufacturing cost.

Measure to Solve the Problem

The present invention includes a first aspect relating to the wearing article and a second aspect relating to a method of making the same. According to the present invention on its first aspect, there is provided an improvement in a wearing article comprises a chassis having longitudinal direction and transverse direction, an inner side facing the skin of a wearer and an outer side facing wearer's garment, a first waist region defined by one of front and rear waist regions, a second waist region defined by the other of the front and rear waist regions and a crotch region extending between the first and second waist regions, and a mechanical fastener including first engagement regions formed in a pair of first lateral zones of said first waist region which are opposed to in the transverse direction and extending in the longitudinal direction and having a mechanical fastener function and second engagement regions formed in a pair of second lateral zones of said second waist region which are opposed to each other in the transverse direction and extending in the longitudinal direction and having a mechanical fastener function and adapted to be detachably engaged with said first engagement regions, wherein the first engagement regions include hook elements and the second engagement regions include loop elements.

The improvement according to the present invention on the first aspect thereof is characterized in that the hook elements comprises a base layer bonded to the chassis, shanks vertically extending upward from the base layer and heads formed on respective distal ends of the shanks and a plurality of deformed regions are intermittently formed over the entire area of array of the hook elements in which at least the heads of the hook elements have been deformed under a pressure-treatment.

According to one preferred embodiment, the deformed regions comprise a plurality of stripes extending in the transverse direction and spaced one from another in the longitudinal direction.

According to another preferred embodiment, the shank also has been deformed under a pressure-treatment in the deformed regions.

According to still another preferred embodiment, bonding means is interposed between the hook elements and the chassis so that the hook elements may be bonded to the chassis via the bonding means.

According to yet another preferred embodiment, the first engagement regions respectively include mount members and the hook elements are attached to the chassis via the mount members.

According to the second aspect of the present invention, there is provided an improvement in a method of making the wearing article as defined by the first aspect of the present invention, comprising the steps of forming the bonding means on at least one of the first engagement regions of the chassis and the hook elements, placing the base layer of the hook elements upon each of the first engagement regions, and subjecting the first engagement regions and the hook elements together to pressure-treatment to create the deformed regions in the hook elements.

According to one preferred embodiment of the invention on its second aspect, further including, prior to pressure-treating the first engagement region and the hook element, steps of bringing the hook elements in engagement with the loop elements and bonding the base layer of the hook elements to the first engagement regions, and folding the chassis in two so that the first and second waist regions would be placed upon each other and bonding respective base layers of the loop elements to the second engagement regions.

Effect of the Invention

The hook elements comprises a base layer bonded to the chassis, shanks vertically extending upward from the base layer and heads formed on respective distal ends of the shanks wherein a plurality of deformed regions are intermittently formed over the entire area of arrays of the hook elements in which at least the heads of the hook elements have been deformed under a pressure-treatment. These deformed regions serve to reinforce the engagement between the hook elements and the loop elements. The deformed regions intermittently created over the entire area of the arrays of the hook elements is advantageous in comparison with the case in which the deformed region must be locally created in specified spots since a relatively high accuracy will be required in the latter case.

The deformed regions are created in the form of stripes and thereby dispersed over the entire area of the arrays of the hook elements. Consequently, the engagement strength between the hook elements and the loop elements are reinforced over the entire area of these arrays.

The shanks also are deformed under a pressure-treatment and the engagement strength between the hook elements and the loop elements are correspondingly further reinforced.

Appropriate bonding means is interposed between the hook elements and the respective first engagement regions so that the hook elements would be bonded to the first engagement regions via the bonding means. By creating the deformed regions after the hook elements have been bonded to the chassis, the engagement strength between the hook elements and the chassis can be reinforced upon creation of the deformed regions.

The hook elements are attached to the chassis via the mount members and the mount members which are prepared separately of the chassis can be used. In consequence, it is possible to extend these mount members outward from the chassis and thereby to facilitate the hook element and the loop element to be engaged with each other.

The step of forming the bonding means on the first engagement regions or on the arrays of the hook elements, the step of placing the base layers of the respective arrays of the hook elements upon the first engagement regions wherein the first engagement regions or the arrays of the hook elements are previously coated with the bonding means, and the step of subjecting the first engagement regions and the hook elements together to the pressure-treatment to create the deformed regions are continuously carried out. In this way, the deformed regions can be created in the course of making the wearing article.

The deformed regions are created after the hook elements have been engaged with the loop elements. In consequence, the engagement between the hook elements and the loop elements becomes further tight.

BRIEF DESCRIPTION OF THE DRAWINGS

FIG. 5 is a sectional view of an engaged assembly.
FIG. 6 is a perspective view of a roller pair.

IDENTIFICATION OF REFERENCE NUMERALS USED IN THE DRAWINGS

Figure 1:
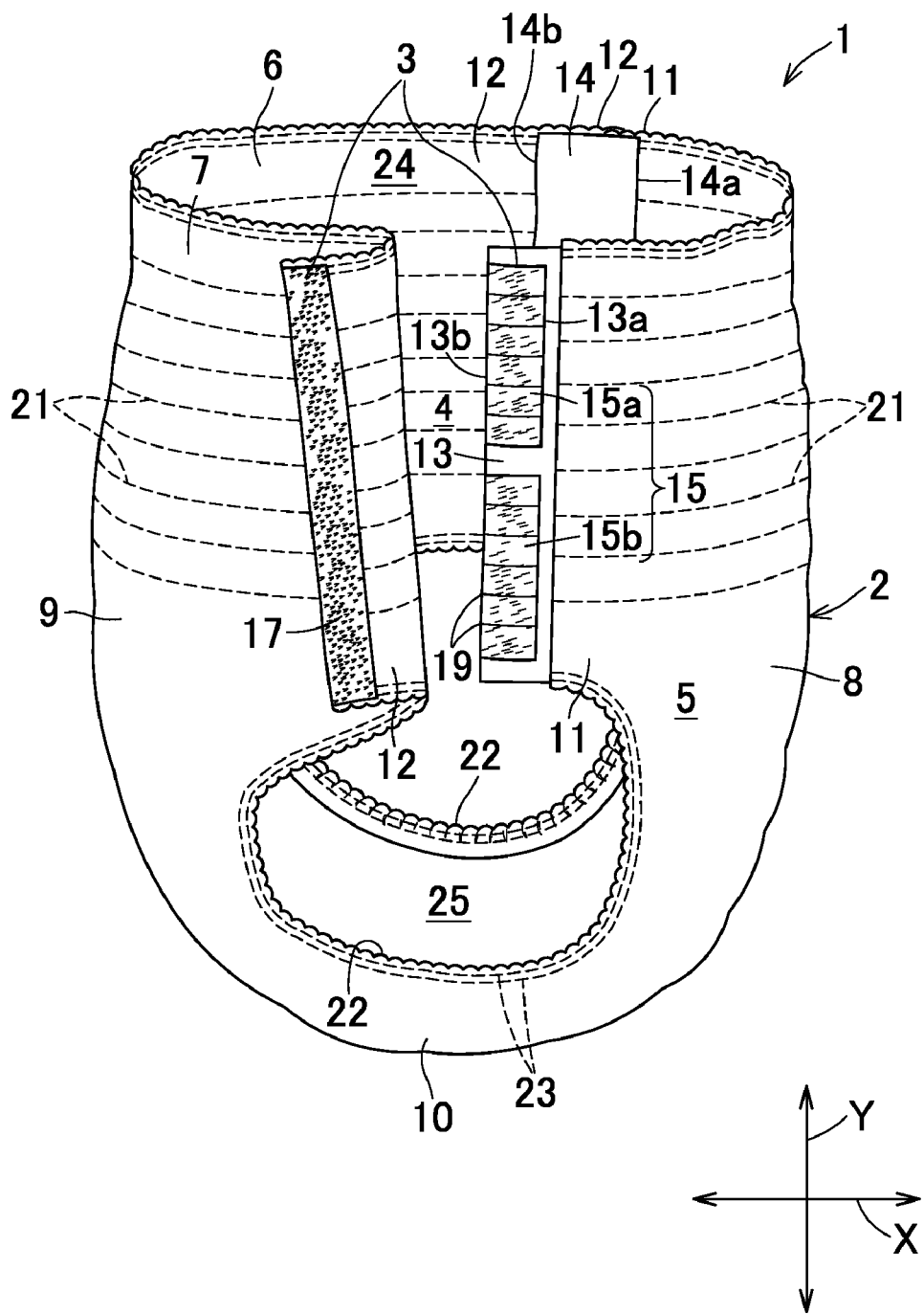
FIG. 1 is a perspective view of a diaper.

1 diaper
2 chassis
3 mechanical fastener
4 inner side facing the skin of a wearer
5 outer side facing a garment
6 inner sheet
7 outer sheet
8 front waist region
9 rear waist region
10 crotch region
11 first lateral zone
12 second lateral zone
13 mount member
14 mount member
15 hook element
16 hook element
17 loop element
18 loop element
19 deformed region
26 base layer
27 shank
28 head

DETAILED DESCRIPTION OF THE PREFERRED EMBODIMENTS

Figure 2:
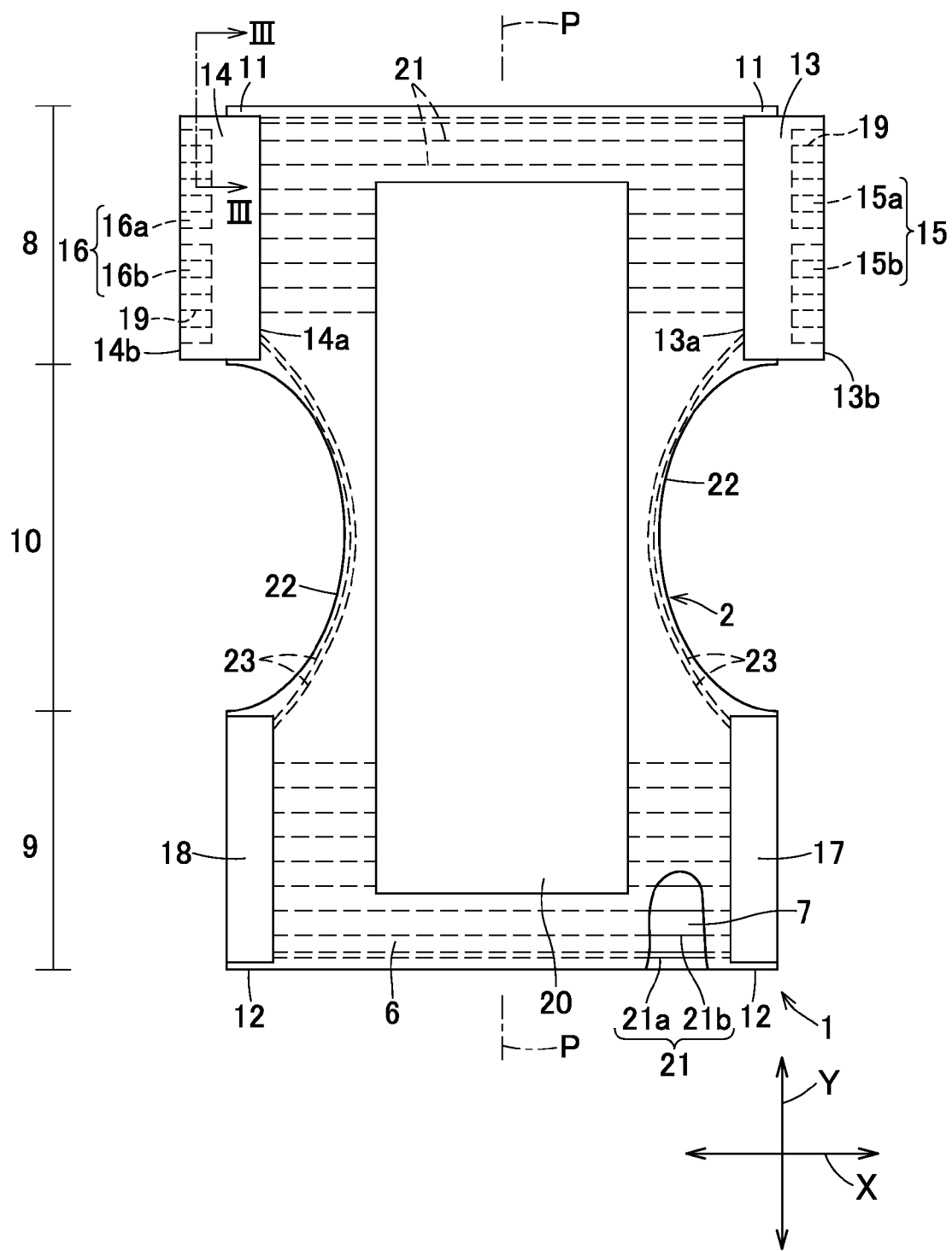
FIG. 2 is a plan view showing the diaper of FIG. 1 as has been flatly developed.
Figure 3:
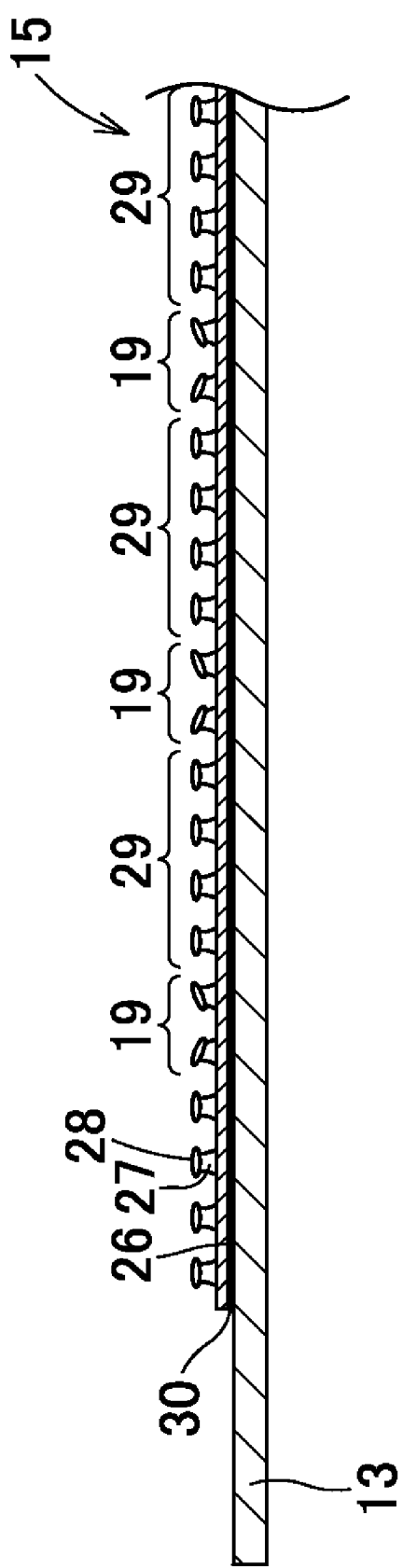
FIG. 3 is a sectional view taken along the line III-III in FIG. 2.

FIGS. 1 through 3 illustrate a diaper for adult as one embodiment of the present invention wherein FIG. 1 is a perspective view of the diaper 1 as put on the wearer and one of opposite side edges of the diaper 1 left opened, FIG. 2 is a flatly developed plan view of the diaper 1 as partially broken away for convenience of illustration, and FIG. 3 is a sectional view taken along the line III-III in FIG. 2. As shown, the diaper 1 includes a chassis 2 having a liquid-absorbing ability and mechanical fasteners 3. The chassis 2 has a longitudinal direction Y, a transverse direction X, an inner side 4 facing the skin of the wearer, an outer side 5 facing a garment worn by the wearer. The chassis 2 comprises an inner sheet 6 defining the inner side 4 facing the skin of a wearer, an outer sheet 7 defining an outer side 5 facing the garment and a liquid-absorbent core 20 sandwiched between these inner and outer sheets 6, 7. The inner sheet 6 may be formed, for example, of a liquid-pervious fibrous nonwoven fabric, the outer sheet 7 may be formed, for example, of a liquid-impervious plastic film and the liquid-absorbent core 20 may be formed, for example, from a mixture of fluff pulp and super-absorbent polymer particles. These stock materials have conventionally been used in the relevant technical field. The chassis 2 comprises a front waist region 8, a rear waist region 9 and a crotch region 10 extending between these two waist regions 8, 9.

The front waist region 8 has a pair of first lateral zones 11 opposed to each other in the transverse direction X and extending in the longitudinal direction Y while the rear waist region 9 has a pair of second lateral zones 12 opposed to each other in the transverse direction X and extending in the longitudinal direction Y. The first lateral zones 11 include mount members (ear-like members) 13, 14, respectively. The inner sheet 6 is provided along the respective first lateral zones 11 with mount members (ear-like members) 13, 14, respectively, which are elongated in the longitudinal direction Y. Via these mount members 13, 14, arrays of hook elements 15, 16 constituting the respective mechanical fasteners are attached to the chassis 2 so as to form first engagement regions, respectively. Each of these mount members 13, 14 may be formed, for example, of a fibrous nonwoven fabric having one of the side edges 13a or 14a bonded to the associated first side edge 11 by adhesives, thermal bonding or ultrasonic bonding means and the other side edge 13b or 14b extending outward from the associated first side edge 11 in the transverse direction X. These portions of the mount members 13, 14 extending outward are provided on respective outer sides facing the garment with the arrays of the hook elements 15, 16 bonded thereto by adhesives, thermal bonding or ultrasonic bonding means. The arrays of the hook elements 15, 16 are respectively divided in upper and lower sub-arrays 15a, 16a and 15b, 16b, respectively, and each pair of the upper and lower sub-arrays is spaced from each other.

The mount members 13, 14 respectively have a length dimension substantially the same as the dimension of the first lateral zones 11 as measured in the longitudinal direction Y and the arrays of hook elements extend to cover substantially over the entire area of the respective mount members 13, 14 in the longitudinal direction Y. More specifically, the arrays of hook elements 15, 16 extend in the longitudinal direction Y leaving slight spaces between ends of the mount members 13, 14 opposite in the longitudinal direction Y and the upper and lower sub-arrays 15a, 16a and 15b, 16b as well as between these upper and lower sub-arrays 15a, 16a and 15b, 16b. Initially, the front and rear waist regions 8, 9 have substantially the same width dimensions in the transverse direction X. After the mount members 13, 14 have been attached to the respective first lateral zones 11 of the front waist region 8, the width dimension of the front waist region 8 as measured in the transverse direction X became larger than the width dimension of the rear waist region 9 as measured in the transverse direction X substantially by width dimensions of the mount members 13, 14. While differentially dimensioning the front and rear waist regions 8, 9 in the transverse direction X in this manner is preferable in the course of sequentially folding up the wearing article as will be described later, such dimensioning is not essential.

The inner sheet 6 is formed along the second lateral zones 12 of the rear waist region 9 with second engagement regions in which arrays of loop elements 17, 18 are attached to the inner sheet 6 by adhesives, thermal bonding or ultrasonic bonding means. The arrays of loop elements 17, 18 respectively have a length dimension of substantially the same as a dimension of the second lateral zones 12 of the rear waist region 9 as measured in the longitudinal direction Y and extend to cover substantially over the entire area of the second engagement regions in the longitudinal direction Y. The arrays of hook elements 15, 16 and the arrays of loop elements 17, 18 are adapted to be detachably engaged one with another and, as these hook elements 15, 16 and loop elements 17, 18, "Velcro"(trademark) or "Magic Tape" (trademark) widely used in the technical field to which the present invention relates may be effectively used.

Both the first and second arrays of hook elements 15, 16 include deformed regions 19 formed by pressure-treating these arrays of hook elements 15, 16 over the entire areas thereof. The deformed regions 19 are spaced one from another at regular intervals in the longitudinal direction Y and a plurality of such deformed regions 19 extend in the transverse direction X.

As will be understood from FIG. 3, each of the hook elements 15, 16 comprises a base layer 26 bonded to each of the mount members 13, 14, a shank 27 extending upward from the base layer 26 and a head 28 formed on a distal end of the shank 27. The head 28 has a surface area larger than a sectional area of the shank 27 so that the hook element as a whole is mushroom-shaped. The hook element 15, 16 and the loop element 17, 18 are engaged with each other as the head 28 is caught by a loop of the loop element 17, 18.

In non-deformed regions 29 of the arrays of hook elements 15, 16 defined between each pair of the adjacent deformed regions 19, the shank 27 extends substantially at right angle to the base layer 26 and a diametrical plane of the head 28 extends substantially in parallel to the base layer 26. In the deformed regions 19, on the other hand, the shank 27 more or less inflects and the diametrical plane of the head 28 takes an oblique posture with respect to the base layer 26 so that the head 28 and the shank 27 may locally intersect with each other at an acute angle. Such intersection at an acute angle between the axis of the shank 27 and one or more radial lines of the head 28 facilitates the head 28 to be caught by the loop of the associated loop element 17, 18 and/or makes it difficult for the head 28 having been caught by the loop to get off from the loop. In this way, the deformed regions 19 serve to reinforce the effect of engagement between the hook elements 15, 16 and the loop elements 17, 18. The head taking an oblique posture facilitates the hook element 15, 16 to be caught by the loop of the associated loop element 17, 18. In the deformed regions 19, the head 28 of the hook element 15, 16 caught by the loop of the associated loop element 17, 18 makes the effect of engagement between these hook and loop elements further reliable.

The direction as well as the angle in and at which the heads 28 oblique with respect to the base layer 26 may be diversified by pressure-treating the arrays of hook elements in appropriate pattern to obtain the deformed regions 19. By diversifying the direction as well as the angle in and at which the respective heads 28 oblique with respect to the base layer 26, the desired effect of the mechanical fastener can be assured in every situation. Specifically, shear force as well as peel force may be exerted on the hook elements 15, 16 and the loop elements 17, 18 in various directions depending upon a manner in which the diaper 1 is put on wearer's body and/or a wearer's posture. In response to such shear force and peel force, a certain number of the hook elements 15, 16 in the deformed regions 19 may have the heads 28 thereof further tightly caught by the loops of the associated loop elements 17, 18. In this way, the desired tight engagement can be maintained.

The deformed regions 19 occupy an area in a range of 5 to 40% of a total area of the arrays of hook elements 15, 16. While not only the heads 28 but also the shanks 27 are deformed in the deformed regions 19 as far as the embodiment shown in FIG. 3 is the case, it is possible to design the deformed regions 19 in which the heads 28 are deformed so as to oblique with respect to the base layer 26 but the shanks 27 are not deformed. The deformed regions 19 are formed by the pressure-treatment without heating and therefore the hook elements 15, 16 would not be thermally fused and the heads 28 and the shanks 27 would not be fusion bonded together. Should the heads 28 and the shanks 27 be fusion bonded together, the heads 28 to be caught by the loops would melt away and consequently the desired effect of engagement between the hook elements 15, 16 and the loop elements 17, 18 would be seriously deteriorated.

The hook elements 15, 16 are attached to the mount members 13, 14 using an adhesive 30 as the bonding means. After the hook elements 15, 16 have been bonded to the mount members 13, 14, the assembly may be pressurized to form the deformed regions 19 and simultaneously to increase the adhesive force required to bond the hook elements 15, 16 to the mount members 13, 14. Consequentially, the hook elements 15, 16 are prevented from being peeled off from the mount members 13, 14, even an intense peel force is exerted between the hook elements 15, 16 and the mount members 13, 14 as it is tried to disengage the hook elements 15, 16 from the loop elements 17, 18. It should be appreciated that, when the hook elements 15, 16 are heat-treated not together with the mount members 13, 14, any bonding means other than the adhesive 30 may be used. When the adhesive 30 is used as the bonding means, an adhesive of the type adapted to increase its adhesive force under a pressure.

The front and rear waist regions 8, 9 are provided with waist elastic members 21 attached thereto under tension so as to extend in the transverse direction X. More specifically, these waist elastic members 21 comprise first elastic members 21a provided in the vicinity of the peripheral edge of the waist-opening and second elastic members 21b provided aside from the first elastic members 21a toward the crotch region 10. These first and second elastic members 21a, 21b are sandwiched between the inner and outer sheets 6, 7 and attached to at least one of the inner and outer sheets 6, 7 by adhesives, thermal bonding or ultrasonic bonding means. The waist elastic members 21 are formed of a plurality of thread-, strand- or tape-like rubber elements wherein the second elastic members 21b are placed substantially at regular intervals in the longitudinal direction Y practically over the entire area of the front and rear waist regions 8, 9 so as to elasticize the front and rear waist regions 8, 9 in the transverse direction X. The front and rear waist regions 8, 9 elasticized in this manner ensure desired fitness of the front and rear waist regions 8, 9 to prevent bodily fluids such as urine from leaking out and at the same time to improve appearance of the article put on the wearer.

In the front waist region 8, the waist elastic members 21 extend in the transverse direction X to respective inner sides of the mount members 13, 14 without intersecting with the mount members 13, 14. The arrays of hook elements 15, 16 are placed in the respective regions of the mount members 13, 14 extending outward from the side edges of the front waist region 8 and therefore the waist members 21 do not overlap the arrays of hook elements 15, 16. In the rear waist region 9 also, the waist members 21 extend to the innermost side edges of the arrays of loop elements 17, 18 and do not intersect with these arrays of loop elements 17, 18. In this way, the arrays of hook elements 17, 18 as well as the arrays of loop elements 17, 18 can be prevented from getting wrinkled under contraction of the waist elastic members 21. In consequence, a desired area of engagement can be prevented from being reduced and the engagement can be prevented form becoming unstable due to formation of wrinkles. It is assured therefore that the hook elements 15, 16 and the loop elements 17, 18 can be kept in secure engagement.

Between the first pair of lateral zones 11 and the second pair of lateral zones 12 as viewed in the longitudinal direction Y, a pair of leg side edges 22 corresponding to side edges of the crotch region 10 extends so as to curve toward a longitudinal center line P-P bisecting a dimension of the diaper 1 in the transverse direction X. Along the leg side edges 22, leg elastic members 23 are attached under tension to the chassis 2. More specifically, these leg elastic members 23 are sandwiched between the inner and outer sheets 6, 7 and attached to at least one of these inner and outer sheets 6, 7 by adhesives, thermal bonding or ultrasonic bonding means. The leg elastic members 23 are formed of a plurality of thread-, strand- or tape-like rubber elements so that the leg side edges 22 may fit the wearer's thighs under contractile force of these rubber elements and prevent bodily fluids such as urine from accidentally leaking beyond respective peripheral edges of the leg-openings. It is possible without departing from the scope of the invention to use natural rubber or synthetic rubber such as polyurethane, or to replace such natural or synthetic rubber, for example, by an elasticized fibrous nonwoven fabric or a plastic sheet or the other elastic members commonly used in the relevant technical field to which the present invention relates.

In such diaper 1 as has been described above, the loop elements 17, 18 may be engaged with the hook elements 15, 16 to connect the front and rear waist regions 8, 9 with each other, thereby to form a waist-opening 24 and a pair of leg-openings 25 and, in consequence, to make the diaper 1 in pull-on pant-shape. To put this diaper 1 with its front and rear waist regions 8, 9 connected with each other on the wearer, the legs of the wearer may be guided through the waist-opening 24, then through the leg-openings 25 and finally the diaper 1 may be pulled upward. Alternatively, the front and rear waist regions 8, 9 may be put on the front and rear waist regions of the wearer before the front and rear waist regions 8, 9 are connected to each other, then the hook elements 15, 16 may be engaged with the loop elements 17, 18 to connected the front and rear waist regions 8, 9 to each other and thereby to make the diaper 1 in pant-shape. In this way, such diaper 1 is selectively used as the pull-on pant-type diaper and as the open-type diaper.

In any case, the hook elements 15, 16 are divided into the upper sub-arrays 15a, 16a and the lower sub-arrays 15b, 16b and these sub-arrays may be one by one engaged with the arrays of loop elements 17, 18. In this way, operating efficiency can be improved in comparison with the case in which a series of the long hooks are engaged with the loop elements at once. In addition to improvement of the operating efficiency, the manner in which these sub-arrays 15a, 16a and the lower sub-arrays 15b, 16b are one by one engaged with the arrays of loop elements 17, 18 is advantageous from another viewpoint. In fact, when it is desired to correct a misalignment after engagement or when it is desired to release the engagement disengage in order to check whether urination or defecation has occurred or not, the upper or lower sub-array of hook elements may be disengaged from or reengaged with the associated sub-array of loop elements. Such manner of operation is easier than the manner in which the entire array of hook elements is reengaged at once with the array of loop elements.

Now a method of making the diaper as has been described above. As will be apparent from FIG. 4, the chassis 2 of the diaper 1 is obtained from a continuous fibrous web and individual articles are formed by finally cutting this continuous fibrous web. The web is fed in a direction indicated by an arrow A. In a first step (a), a first web 31 adapted to form the outer sheet 7 is fed while the waist elastic members 21 and the leg elastic members 23 are continuously attached under tension in the feeding direction to this first web 31. Bonding means such as adhesives used to attach these elastic members 21, 23 are not shown for convenience of illustration.

In a second step (b), a second web 32 adapted to form the inner sheet 6 is fed onto the first web 31 and these first web 31 and the second web 32 are bonded to each other. In this second step (b) and later, the waist elastic member 21 are not shown and only the leg elastic member 23 will be indicated by dashed lines. In a third step (c), a circular region along the leg elastic member 23 is cut away the first and second webs 31, 32 to forma circular opening 36. A peripheral edge of this opening 36 defines the leg side edges, i.e., the leg side edges. The circular opening 36 is formed on preset cutting line 35 indicated by a dashed line. In a fourth step (d), the liquid-absorbent structure 20 is attached to the second web 32 by not shown bonding means between each pair of the adjacent openings 36 as viewed in the machine direction.

Figure 4:
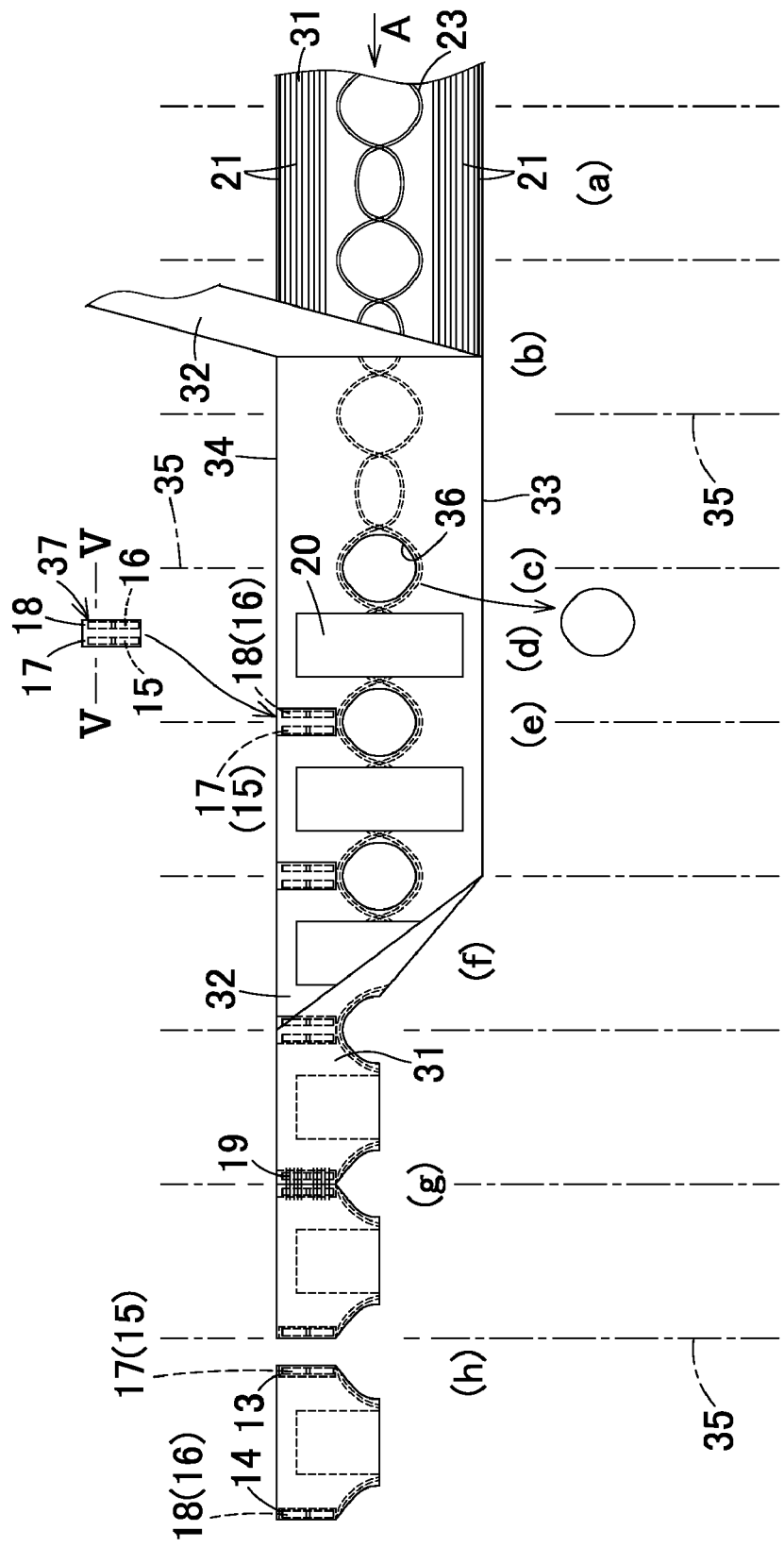
FIG. 4 is a diagram schematically illustrating a method of making the diaper.

In a fifth step (e), an engaged assembly 37 which comprises the hook elements 15, 16, and the loop elements 17, 18 engaged with each other is attached to the second web 32. Specifically, the hook elements 15, 16 are bonded to the mount members 13, 14 and loop elements 17, 18 are engaged with the hook elements 15, 16 to form the engaged assembly 37. FIG. 5 is a sectional view taken along the line V-V in FIG. 4, showing the engaged assembly 37. As illustrated, the mount members 13, 14 are respectively folded in three, and on a surface to which the hook elements 15, 16 are bonded, the mount members 13, 14 are continuous in the machine direction. The loop elements 17, 18 also are continuous in the machine direction. Such engaged assembly 37 is fed to the second web 32. The first and second webs 31, 32 respectively have one end 33 extending in the machine direction and the other end 34 extending in the machine direction. The side on said one end 33 defines the front waist region 8 of the diaper 1 and the side on the other end 34 defines the rear waist region 9 of the diaper 1. The mount members 13, 14 constituting the engaged assembly 37 are bonded to the side on the other end 34 of the second web 32 by bonding means (not shown). Between each of the adjacent hook elements 15, 16 as viewed in the machine direction and between each of the adjacent loop elements 17, 18 as viewed in the machine direction, the first and second webs 31, 32 are finally cut along the preset cutting lines 35 to obtain the individual articles.

In a sixth step (f), the first and second webs 31, 32 are folded in two in the cross direction so that the opposite ends 33, 34 would fall on each other with the liquid-absorbent structure 20, the hook elements 15, 16 and the loop elements 17, 18 would be wrapped inside. The loop elements 17, 18 are previously provided with bonding means (not shown) so that the loop elements 17, 18 would be bonded to the side on said one end 33 as the first and second webs 31, 32 are folded in two.

In a seventh step (g), the hook elements 15, 16 and the loop elements 17, 18 engaged together are pressure-treated from the side of the first web 31 to obtain the deformed regions 19. The pressure-treatment is carried out using a roller pair as shown by FIG. 6. The roller pair comprises a first roller 38 and a second roller 39 wherein the first roller 38 is provided with a press pattern 40 and the second roller 39 has no press pattern. The first and second webs 31, 32 are set so that the side of the hook elements 15, 16 faces the first roller 38 and the side of the loop elements 17, 18 faces the second roller 39. The hook elements 15, 16 are formed with the deformed regions 19 as the first and second rollers 38, 39 rotate. The press pattern 40 comprises a plurality of ridges 41 extending in the machine direction so that these ridges 41 press the hook elements 15, 16 to form the deformed regions 19. In consequence, a plurality of the stripe-like deformed regions 19 are formed so as to extend in the transverse direction X and to be spaced one from another in the longitudinal direction Y. The press pattern 40 is formed on the first roller 38 at the position corresponding to the position at which the hook elements 15, 16 are attached and a clearance between the press pattern 40 and the second roller 39 is set to approximately 0.1 to 2.0 mm. It should be appreciated that such specific clearance has been set for the hook elements 15, 16 each has a thickness of approximately 0.5 mm and the clearance between the press pattern 40 and the second roller 39 may be appropriately selected depending on various factors such as thickness and stiffness of the hook elements 15, 16 and the other members.

In a eighth step (h), the first and second webs 31, 32 folded together in two are cut along the preset cutting line 35 and thereby the individual diaper 1 is obtained.

The diapers 1 are formed from these continuous first and second webs 31, 32 and simultaneously the hook elements 15, 16 as well as the loop elements 17, 18 are attached thereto so as to form the deformed regions 19. In this way, the production speed can be significantly improved. In the course of making the diaper 1, the hook elements 15, 16 and the loop elements 17, 18 can be tightly engaged with each other. In this way, these elements would not be more or less displaced from the proper engagement or disengaged from each other in the course of manufacturing or before actual use of the diaper 1.

According to the illustrated embodiment of the invention, after the hook elements 15, 16 have been attached to the mount members 13, 14 and the loop elements 17, 18 have been engaged with the hook elements 15, 16 to form the engaged assembly 37, this engaged assembly 37 is attached to the second web 32 adapted to form the chassis 2. However, it is also possible to put the hook elements 15, 16 into engagement with the loop elements 17, 18 by folding the first and second webs together into after the hook elements 15, 16 have been attached to the side of the other end 34 of the second web 34 and the loop elements 17, 18 have been attached to the side of the one end 33 of the second web 34.

According to the illustrated embodiment, the inner and outer sheets 6, 7 formed of the first and second webs 31, 32, the hook elements 15, 16 and the loop elements 17, 18 are laminated to be pressurized by the first and second rollers 38, 39. Instead, it is possible to pressurize the hook elements 15, 16 independently or the inner and outer sheets 6, 7 laminated with the hook elements 15, 16 to be pressurized by the rollers 38, 39. However, preferably the assembly of the hook elements 15, 16 and the loop elements 17, 18 engaged with each other may be pressurized to make the engagement of them further tight.

While the stripe-like press pattern 40 is used in the illustrated embodiment, the other press pattern such as circular or square dot-like press pattern or wavy press pattern also may be used as far as the deformed regions can be formed in arrays of the hook elements 15, 16. Creation of the deformed regions 19 by the first and second rollers 38, 39 enables the first and second webs being fed to be pressure-treated continuously. While the first roller 38 is formed with the press pattern 40 according to the illustrated embodiment, the second roller 39 also may be provided with a pattern operatively associated with the press pattern 40. For the method of making the diaper 1 as has been described above, various timings such as timing to feed the liquid-absorbent structure 20 or timing to form the circular opening corresponding to the leg side edges may be appropriately varied.

While the illustrated embodiment employs the mushroom-shaped hook elements 15, 16, more conventional hook elements, for example, fishhook-shaped hook elements also may be used. In any case, the head of the hook element may be deformed by the pressure-treatment and thereby the orientation of the hook element may be made random to assure the tight engagement with the associated loop element. Shape of the deformed region 19 may be varied by regulating a pressure and/or pressurizing period depending on the associated loop element.

While the hook elements 15, 16 are attached to the front waist region 8 and the loop elements 17, 18 are attached to the rear waist region 9 according to the illustrated embodiment, such relationship may be reversed. More specifically, instead of designating the front waist region 8 as the first waist region and designating the rear waist region 9 as the second waist region, it is also possible to designate the front waist region 8 as the second waist region and to designate the rear waist region 9 as the first waist region. In any case, it is desired to attach the hook elements having a relatively high stiffness to the article so as to prevent these hook elements from coming in contact with the skin of a wearer. This is important in order to prevent the hook elements from damaging the skin of the wearer. While the diaper 1 according to the illustrated embodiment is provided with the liquid-absorbent core 20 separately with the chassis 2, the liquid-absorbent core 20 also can be interposed between the inner and outer sheets 6, 7 of the chassis 2.

While the first lateral zones 11 respectively include the mount members 13, 14 and the hook elements 15, 16 are attached to the chassis 2 via these mount members 13, 14 according to the illustrated embodiment, it is possible to attach the hook elements 15, 16 directly to the chassis 2. In this case, the hook elements 15, 16 may be bonded to the outer sheet 7 in the front waist region 8 and the cost due to providing the mount members 13, 14 can be saved.

The invention claimed is:

1. A wearing article which comprises:
   a chassis having longitudinal direction and transverse direction;
   an inner side facing the skin of a wearer and an outer side facing a garment worn by the wearer;
   a first waist region defined by one of front and rear waist regions;
   a second waist region defined by the other of said front and rear waist regions;
   a crotch region extending between said first and second waist regions; and
   a mechanical fastener including first engagement regions formed in a pair of first lateral zones of said first waist region which are opposed to in said transverse direction and extending in said longitudinal direction and having a mechanical fastener function and second engagement regions formed in a pair of second lateral zones of said second waist region which are opposed to each other in said transverse direction and extending in said longitudinal direction and having a mechanical fastener function and adapted to be detachably engaged with said first engagement regions, wherein said first engagement regions include hook elements and said second engagement regions include loop elements,
   said hook elements comprise a base layer bonded to said chassis, shanks vertically extending upward from said base layer and heads formed on respective distal ends of said shanks and a plurality of deformed regions are intermittently formed over the entire area of array of said hook elements in which at least said heads of said hook elements have been deformed under a pressure-treatment along the entire extent of the deformed region, wherein said deformed regions comprise a plurality of stripes extending continuously in said transverse direction from a first longitudinal outer edge of the first engagement region to a second longitudinal outer edge of the first engagement region, and space apart from one another in said longitudinal direction.

2. The wearing article as defined by claim 1, wherein said shank also has been deformed under a pressure-treatment in said deformed regions.

3. The wearing article as defined by claim 1, wherein bonding means is interposed between said hook elements and said chassis so that said hook elements may be bonded to said chassis via said bonding means.

4. The wearing article as defined by claim 1, wherein said first engagement regions respectively include mount members and said hook elements are attached to said chassis via said mount members.

5. A method of making the wearing article as defined by claim 1, comprising the steps of:
   forming said bonding means on at least one of said first engagement regions of said chassis and said hook elements;
   placing said base layer of said hook elements upon each of said first engagement regions; and
   subjecting said first engagement regions and said hook elements together to pressure-treatment to create said deformed regions in said hook elements.

6. The method of making the wearing article as defined by claim 5, further including, prior to pressure-treating said first engagement region and said hook element, the steps of:
   bringing said hook elements in engagement with said loop elements and bonding said base layer of said hook elements to said first engagement regions; and folding the chassis in two so that said first and second waist regions would be placed upon each other, and bonding respective base layers of said loop elements to said second engagement regions.

7. The wearing article as defined by claim 1, wherein said shank also has been deformed under a pressure-treatment in said deformed regions.

8. The wearing article as defined by claim 1, wherein bonding means is interposed between said hook elements and said chassis so that said hook elements may be bonded to said chassis via said bonding means.

9. The wearing article as defined by claim 2, wherein bonding means is interposed between said hook elements and said chassis so that said hook elements may be bonded to said chassis via said bonding means.

10. The wearing article as defined by claim 7, wherein bonding means is interposed between said hook elements and said chassis so that said hook elements may be bonded to said chassis via said bonding means.

11. The wearing article as defined by claim 1, wherein said first engagement regions respectively include mount members and said hook elements are attached to said chassis via said mount members.

12. The wearing article as defined by claim 2, wherein said first engagement regions respectively include mount members and said hook elements are attached to said chassis via said mount members.

13. The wearing article as defined by claim 3, wherein said first engagement regions respectively include mount members and said hook elements are attached to said chassis via said mount members.

14. The wearing article as defined by claim 7, wherein said first engagement regions respectively include mount members and said hook elements are attached to said chassis via said mount members.

15. The wearing article as defined by claim 8, wherein said first engagement regions respectively include mount members and said hook elements are attached to said chassis via said mount members.

16. The wearing article as defined by claim 9, wherein said first engagement regions respectively include mount members and said hook elements are attached to said chassis via said mount members.

17. The wearing article as defined by claim 10, wherein said first engagement regions respectively include mount members and said hook elements are attached to said chassis via said mount members.

* * * * *